United States Patent [19]

Dolan

[11] 4,224,595

[45] Sep. 23, 1980

[54] GRADED PARTICLE ADSORPTION TYPE SENSOR AND METHOD OF IMPROVING PERFORMANCE OF AN ADSORBING SENSOR

[75] Inventor: James P. Dolan, Seattle, Wash.

[73] Assignee: ADS Systems, Inc., Seattle, Wash.

[21] Appl. No.: 957,174

[22] Filed: Nov. 2, 1978

[51] Int. Cl.² .............................................. H01L 7/00
[52] U.S. Cl. ...................................... 338/34; 422/88; 422/98
[58] Field of Search ............... 338/13, 34, 35; 422/88, 422/98; 23/230 E; 73/27, 73

[56] References Cited

U.S. PATENT DOCUMENTS

| | | | |
|---|---|---|---|
| 1,559,461 | 10/1925 | Ruben | 338/34 X |
| 3,045,198 | 7/1962 | Dolan et al. | 338/13 |
| 3,767,519 | 10/1973 | Kojima et al. | 252/512 |

Primary Examiner—C. L. Albritton
Attorney, Agent, or Firm—Seed, Berry, Vernon & Baynham

[57] ABSTRACT

An adsorbing type sensor of the type having electrically conductive adsorbent particles resiliently embedded in a surface and forming an electrical conductive path through the sensor, the resistance of which or in one embodiment current through which varies in response to the presence of an adsorbate medium exposed to the particles and in which the adsorbent particles are of varying sizes interspersed among one another and a method of increasing the sensitivity and range of an adsorbing type sensor by interspersing various sized abutting adsorbent particles.

6 Claims, 7 Drawing Figures

GRADED PARTICLE ADSORPTION TYPE SENSOR AND METHOD OF IMPROVING PERFORMANCE OF AN ADSORBING SENSOR

BACKGROUND OF THE INVENTION

1. Field of the Invention

This invention pertains to sensors of the type which change resistivity or current in a circuit in response to the presence of an adsorbate medium gas or liquid.

2. Description of the Prior Art

U.S. Pat. No. 3,045,198 describes an adsorption type detection device which employs electrically conductive adsorbent particles resiliently attached to a surface with an electrical conductive path being formed through the particles. These particles will, due to adsorption forces in absorbates of greater than about 9.0 Van der Waals Constant, become separated in the presence of an adsorbate medium to change the resistivity through the electrical conductive path in the sensor. The adsorbent particles used and described in U.S. Pat. No. 3,045,198 are of substantially uniform size such as 0.001 inch mean diameter. This uniform size was considered to be a requirement for an effective sensor.

U.S. pending patent application Ser. No. 841,802, filed Oct. 13, 1977 discloses another type sensor also using adsorbent particles. In this sensor a voltage is applied to the sensor to a level at which the current no longer increases linearly. When exposed to an adsorbate of Van der Waals Constant values below or above about 9.0 the current through the sensor or voltage across the sensor changes to a new level in the non linear region.

SUMMARY OF THE INVENTION

It is an object of this invention to provide a method and apparatus for improving the sensitivity and range of an adsorbing type sensor.

It is another object of this invention to provide a method and apparatus for improving the response of an adsorbing type sensor.

Basically, the objects of this invention are achieved by interspersing with one adsorbent particle size, one or more different sized adsorbent particles all in electrically conductive contact with one another and attaching all of these particles in a manner such that the resilient force anchoring the particles against movement differs dependent upon the size of the particle so that the Van der Waal's adsorption forces will cause the various particles to separate at different times and produce greater changes in resistivity, current through the sensor or voltage across the sensor, respond to a greater range of Van der Waal's constant adsorbate mediums, and be more sensitive by responding to lower concentrations of adsorbate medium.

DESCRIPTION OF THE PREFERRED EMBODIMENTS

Figure 1:
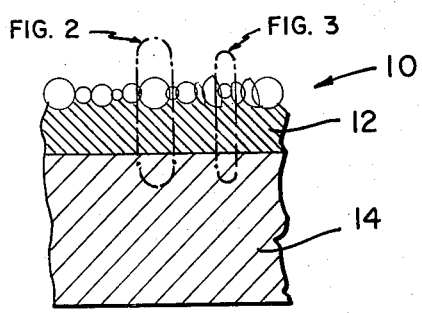
FIG. 1 is a fragmentary, schematic section of an adsorbing type sensor generally of the type shown in U.S. Pat. No. 3,045,198 embodying the principles of this invention.
Figure 2:
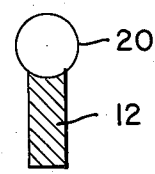
FIG. 2 is a detail of a large particle embodied in the sensor of FIG. 1.
Figure 3:
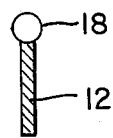
FIG. 3 is a detail of a small particle embodied in the sensor of FIG. 1.

Adsorbent particles 10 are generally attached to a resilient material 12 as described in U.S. Pat. No. 3,045,198 or preferably are embedded in a layer of silicon rubber product such as manufactured by General Electric Company under the trademark "Bathtub Seal". This silicon coating is applied to the surface of a rigid base 14 which may be a conventional cylindrical resistor and then after becoming tacky the sensor is rolled gently through a pile of adsorbent particles. After the silicon rubber has set to the point where the particles are permanently anchored the sensor is ready to be used in a detection circuit. It is an important part of this invention that the pile of adsorbent particles used have a preferred range of particle size from 0.5 microns to about 500 microns but particle size ranges from 0.1 microns to as large as 1,000 microns may be employed successfully. These particles may be hand ground such as by using a mortar and pestle and are intermixed together. The particles may be obtained by mixing various commercially available graded sizes of a single material such as powdered graphite or by mixing combination of commercially available particles such as finely ground silver representing the larger particle size with the powdered graphite representing the smaller particle size. Combinations of silver particle sizes and platinum black size particles is another example. The most practical sizing is a multiple sized graphite particle that ranges from 50 micron to as large as 500 microns. FIG. 3 illustrates schematically a small 50 micron particle 18 whereas FIG. 2 illustrates schematically a larger 500 micron particle 20 with it being understood that the particles 10 will have additional interspersed particles of sizes between the 50 and 500 microns.

It is believed that the particles because of the surface area with which they are attached to the resilient material 12 causes them to have a spring force against movement toward and away from each other which varies with the magnitude of the surface area of attachment. Large particles 20, therefore, having a large surface area in contact with the resilient material will be relatively stiff against movement whereas small particles 18 having a small area of contact in the resilient material will be much more flexible. This achieves several benefits: First, in the presence of an adsorbate medium, the Van der Waal's forces trying to separate the particles will separate smaller particles first due to their lower spring force producing a change in resistivity of the sensor, a change in current through the sensor, or a change in voltage across the sensor through the electrical conductive path of the particles at lower concentrations of the adsorbate medium. Secondly, in high concentrations of the adsorbate medium, the smaller size particles will still begin to separate at an earlier time than the larger sized particles so that the change in resistivity of the electrically conductive particles will be a smoother increasing curve rather than a stepped curve as is found sometimes with particles all of a uniform size. That is, uniform sized particles sometimes react like a switch such that the resistance does not change appreciably until all of the particles separate at about the same time at which time there is a pronounced change in resistivity. Thirdly, the total range of resistivity of the sensor, current or voltage is increased because the particles of different sizes begin to separate at a very short time after exposure to the adsorbate medium and continue to separate after exposure to a large quantity of the medium so that the resistivity, current or voltage changes do not terminate at an early saturation level but continue to increase to a much greater saturation level. It is contemplated that the sensor in addition to the above advantages can differentiate by changes in resistivity, current or voltage between different types of adsorbate mediums, such as two different gases, and can differentiate between different volumes of the adsorbate.

Figure 4:
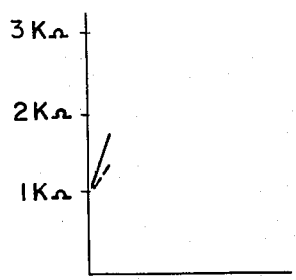
FIG. 4 is a graph comparing graded and uniform sized particle sensors in the presence of a small quantity of isopropyl alcohol adsorbate medium.

Examples of comparison tests between the uniform size sensor described in U.S. Pat. No. 3,045,198 and Ser. No. 841,802 and the improved graded sized sensor are illustrated in the drawings. FIG. 4 is a comparison of a graded graphite particle sized sensor (solid line) with a uniform particle sized sensor (dotted line). (All graded size particle tests below were with #2 powdered flake graphite having a particle size varying from 0.1 to 1000 microns. All uniform size particle tests were with carbon particles about 15 microns in diameter.) Both sensors were exposed to 100 microliters of isopropyl alcohol vapor for one minute in a two liter container. The Van der Waal's constant for isopropyl alcohol is approximately 14.92. The graded sensor increased from an air resistivity of 1000 ohms to 1750 ohms whereas the uniform particle sized sensor rose from 1000 ohms air resistance to 1250 ohms.

Figure 5:
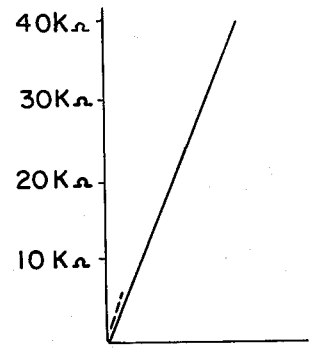
FIG. 5 is a similar graph comparing a graded and a uniform sized sensor in a small quantity of adsorbate medium of gasoline having a relatively high Van der Waal's Constant of approximately 32.

FIG. 5 illustrates a similar comparison between a graded (solid line) and a uniform particle sized sensor (dotted line) for three minute exposures to gasoline vapor having a Van der Waal's constant of approximately 32 in a two liter container. In this example the resistance of the uniform form sized particle sensor went from 1.84 K ohms in air to 4.0 K ohms and the graded particle sized sensor went from 0.978 K ohms in air to 40.8 K ohms approximately twenty times as increase in range.

Figure 6:
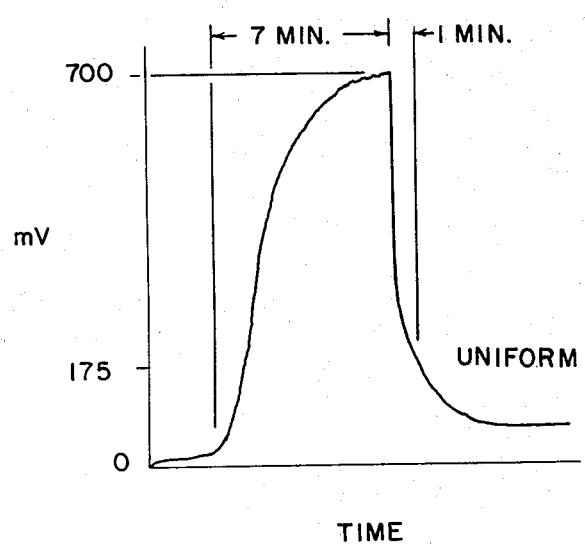
FIGS. 6 and 7 are comparisons of uniform and graded particle adsorbing sensors, respectively, both in 40 microliters of trichloralethylene.
Figure 7:
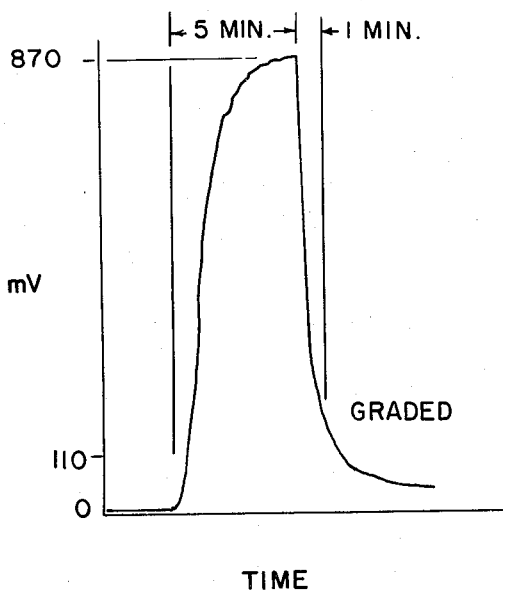

FIGS. 6 and 7 show comparisons of a uniform particle size sensor (FIG. 6) with a graded particle sized sensor (FIG. 7). Both sensors were exposed to 40 microliters of trichloralethylene in a three liter container. The uniform sized particle sensor varied from approximately 0 millivolts (in air) to 700 millivolts measured across the sensor reaching a peak at 700 millivolts while the graded particle sized sensor made a change from approximately 0 to 870 millivolts. The graded particle sized sensor took five minutes approximately to reach its peak point while the uniform particle sized sensor took approximately seven minutes to reach its peak adsorption point. Of interest and an important consideration is that the sensors when removed from the trichloralethylene and placed back in air began to desorb, that is, lose the adsorbate, but the graded particle sensor desorbed much more rapidly and further than the uniform particle sized sensor in the same period of time. The graded particle sensor dropped 760 millivolts in one minute while the uniform particle sized sensor dropped only 525 millivolts in the same one minute period. The curve at the bottom of the desorption time in FIG. 6 shows that the graded particle sized sensor desorbed further and in a much sharper curve than a uniform size particle. This phenomenon of more rapid desorption is particularly advantageous in detection circuits, such as for medical anesthetic detection, when it is desirable that the sensor be brought down to a very low attached adsorbate level so that repeated tests from base line using the sensor can be carried out with only a short desorption time delay between the tests.

Additional tests are shown in the following table for gases in a three liter container:

|  | Approx. Van der Waal's Constant | Graded Particles | | Uniform Particles | |
| --- | --- | --- | --- | --- | --- |
| Air |  | 2.75 | ma | 2.87 | ma |
| Methane | 2.2 | +0.10 | ua change | +0.01 | ua change |
| Acetylene | 4.39 | −10. | ua change | −10. | ua change |
| 50 ul Trichloroethane | 24 | −180. | ua change | −55. | ua change |
| 40 ul Halothane | 17–24 | −90. | ua change | −30 | ua change |
| 80 ul Halothane | 17–24 | −270. | ua change | −90. | ua change |

Gases such as methane and acetylene having relatively low Van der Waal's contants and in very low concentrations, as above, which were exposed to the sensor in air at rate of about ½ cubic foot per hour, did not show an appreciable change between the graded size particles and the uniform sized particles indicating a lower threshold of reliable enhancement from the use of a graded sensor. Where Van der Waal's constants were higher, however, for trichloroethane and Halothane change in current through the sensor were much greater in the graded particle sized sensor. It sould be understood that the Van der Waal's constant chosen for Halothane is estimated as falling between 17 and 24 since tabulated data on this gas is not yet available in reference texts.

For higher concentrations of even the low Van der Waals constant gases, such as acetylene in a two liter container, the graded particle size sensor did show greater changes as shown below.

|  |  | Graded | | Uniform | |
| --- | --- | --- | --- | --- | --- |
| Air |  | 2.7 | ma | 2.75 | ma |
| 40 ul Acetylene | 4.39 | 90 | ua | 15 | ua |
| 80 ul Acetylene | 4.39 | 270 | ua | 90 | ua |

In another test two sensors were picked, both with the same air base resistance of 650 ohms. Each sensor was attached to a resistance measuring device and the sensor was inserted into a two liter container. A specific amount of 1,1,1,trichloroethane to the amount of 10 microliters was exposed to the sensors. The sensor with uniform particle sizes increased from 650 ohms air to 1200 ohms or double its air base resistance. The 650 ohms graphite sensor with the graded size particles went to 10,000 ohms or 12.5 times its air base resistance.

The resistance range of the graded size particle sensor was thus about six times that of the uniform sized particle sensor.

While the preferred embodiments of the invention have been illustrated and described, it should be understood that variations will be apparent to one skilled in the art.

I claim:

1. An adsorbing sensor of the type having electrically conductive adsorbent particles resiliently embedded in a surface and forming an electrical conductive path through the sensor the resistance of which varies in response to the presence of an adsorbate medium exposed to the particles, the improvement comprising:

first adsorbent particles of a first size attached to said surface, extending outwardly from the surface in a position to be exposed to the adsorbate medium, and having a resilient anchoring force against movement of a first low magnitude, a plurality of adsorbent particles of additional sizes interspersed with said first particles, attached to said surface, extending outwardly from the surface in a position to be exposed to the adsorbate medium, and having a resilient anchoring force against movement of magnitudes different than said first lower magnitude, said first and additional sized particles engaging one another externally of said surface to form said electrical conducting path, and whereby absorption forces which cause the adsorbate to force the particles apart and thus change the resistance of the conductive path, changes the resistance more smoothly and over a greater range than with one uniform size of particles.

2. The sensor of claim 1, wherein said particles are embedded within said surface and said surface is a resilient medium.

3. The sensor of claim 1, wherein the different sized particles are between 0.1 microns to 1000.0 microns.

4. The sensor of claim 3, wherein the different sized particles are preferably between 0.5 microns to 500 microns.

5. The sensor of claim 1, wherein said particles include a number of additional sizes of particles.

6. A method of increasing the sensitivity and resistivity range of an adsorptive type sensor in which abutting electrically conductive adsorbent particles are resiliently attached to a surface and form an electrical conductive path through the sensor the resistance of which varies in response to changes of an adsorbate medium exposed to the particles, the improvement comprising:

attaching a first set of outwardly protruding, abutting adsorbent particles to said surface with a resilient anchoring force against movement of a first magnitude, attaching a second set of outwardly protruding, abutting adsorbent particles interspersed with and in contact with said first set of adsorbent particles with a second resilient anchoring force against movement of a second magnitude greater than said first magnitude, and exposing the sensor to an adsorbate whereby exposure of the outwardly protruding, abutting particles to the adsorbate will cause the particles to separate different amounts to vary the resistance differently than with particles attached with a uniform anchoring force.

* * * * *